United States Patent
Terashi et al.

(10) Patent No.: US 9,468,451 B2
(45) Date of Patent: Oct. 18, 2016

(54) MEDICAL GUIDE WIRE

(71) Applicant: FMD Co., Ltd., Toda-shi, Saitama (JP)

(72) Inventors: Tsuyoshi Terashi, Toda (JP); Seiji Shimura, Toda (JP)

(73) Assignee: FMD Co., Ltd., Toda-shi, Saitama (JP)

( * ) Notice: Subject to any disclaimer, the term of this patent is extended or adjusted under 35 U.S.C. 154(b) by 0 days.

(21) Appl. No.: 15/042,156

(22) Filed: Feb. 12, 2016

(65) Prior Publication Data
US 2016/0242794 A1 Aug. 25, 2016

(30) Foreign Application Priority Data

Feb. 24, 2015 (JP) ................................. 2015-050010

(51) Int. Cl.
*A61B 17/22* (2006.01)
*A61M 25/09* (2006.01)

(52) U.S. Cl.
CPC ...... *A61B 17/22* (2013.01); *A61B 2017/22001* (2013.01); *A61B 2017/22044* (2013.01); *A61B 2017/22094* (2013.01); *A61M 2025/09083* (2013.01)

(58) Field of Classification Search
CPC .................... A61M 25/0054; A61M 25/0009; A61M 25/09; A61M 25/0053
See application file for complete search history.

(56) References Cited

U.S. PATENT DOCUMENTS

| | | | |
|---|---|---|---|
| 2009/0036834 A1* | 2/2009 | Voeller | A61M 25/0013 604/164.13 |
| 2010/0249654 A1 | 9/2010 | Elsesser et al. | |
| 2011/0251519 A1* | 10/2011 | Romoscanu | A61M 25/0013 600/585 |
| 2012/0041421 A1 | 2/2012 | Nishigishi | |
| 2012/0323145 A1 | 12/2012 | Nagano et al. | |
| 2015/0148706 A1* | 5/2015 | Abner | A61M 25/09 600/585 |

FOREIGN PATENT DOCUMENTS

| | | |
|---|---|---|
| EP | 2417998 A | 2/2012 |
| EP | 2689795 A | 1/2014 |
| JP | H08-317989 A | 12/1996 |
| JP | 4623906 B | 2/2011 |

(Continued)

OTHER PUBLICATIONS

Japanese decision to grant a patent dated Dec. 8, 2015.
Japanese notice of the reason for refusal dated Aug. 25, 2015.
The extended European search report dated Jul. 22, 2016.

*Primary Examiner* — Sean Dougherty
(74) *Attorney, Agent, or Firm* — Yokoi & Co., U.S.A.; Toshiyuki Yokoi

(57) ABSTRACT

A distal end portion 2B of the core has a structure of a combined truncated cone 26 formed by connecting truncated cones satisfying a predetermined relational expression. An outer diameter ratio between the maximum outer diameter and the minimum outer diameter of the combined truncated cone 26 is greater than the outer diameter ratio between a large diameter proximal portion and a small diameter distal portion of an inner coil 4, and is greater than the outer diameter ratio between a large diameter proximal portion and a small diameter distal portion of the outer coil. Because of this, the rotation angle of the proximal side is reduced when rotation operation is performed and the torsional moment toward the distal end side is increased. Thus, the perforation performance at the completely occluded lesion can be improved.

6 Claims, 7 Drawing Sheets

(56) References Cited

FOREIGN PATENT DOCUMENTS

| JP | 2012-034922 A | 2/2012 |
| JP | 2013-000268 A | 1/2013 |
| JP | 5565847 B | 8/2014 |
| WO | 01/36034 A | 5/2001 |
| WO | 2009/039063 A | 3/2009 |

* cited by examiner proximal end side ←→ distal end side

MEDICAL GUIDE WIRE

CROSS-REFERENCES TO RELATED APPLICATIONS

This patent specification is based on Japanese patent application, No. 2015-050010 filed on Feb. 24, 2015 in the Japan Patent Office, the entire contents of which are incorporated by reference herein.

BACKGROUND OF THE INVENTION

1. Field of the Invention

The present invention relates to a medical guide wire used for treatment of a vascular lesion or the like.

2. Description of Related Art

Conventionally, in the treatment of the vascular lesion such as a stenotic portion and a completely occluded portion of a blood vessel, a medical guide wire (hereinafter simply referred to as the guide wire) is used. On the guide wire, a single coil spring or the like is provided on a distal end portion or a coil spring having a double layered structure, including an inner coil into which a core is inserted and an outer coil concentric with the inner coil, is provided. The distal end portion of the guide wire is reached to the vascular lesion such as the stenotic portion and the completely occluded portion of the blood vessel to perform a radial dilation (radial expansion) treatment.

In such a case, since the guide wire is passed through the vascular lesion, a high rotation transmission performance from a proximal end side (rear side) to a distal end side, a perforation performance and a fatigue resistance against continuous use are required.

Patent Document 1 discloses, about the guide wire, a bending rigidity and other properties of the core about a portion located at the proximal end side than the coil spring of the distal end portion.

Patent Document 2 discloses, about the guide wire, the coil spring located at the distal end portion and formed as a double layered structure including an inner coil and an outer coil which are concentric with each other.

[Patent document 1] Japanese Patent No. 4623906
[Patent document 2] Japanese Patent Laid-Open Publication No. 08-317989

BRIEF SUMMARY OF THE INVENTION

In the guide wire disclosed in Patent Document 1, the core is made of a super-elastic metal of stainless steel or nickel-titanium. In the technology disclosed in this document, the bending rigidity of the core is linearly changed in a longitudinal direction at a portion located at the proximal end side than the distal end portion of the coil spring. Thus, resistance is prevented from being increased suddenly, and operability for an operator is improved.

In Patent Document 2, the guide wire has a double layered structure including an inner coil made of a radiopaque wire and an outer coil made of stainless, shape memory alloy or the like. In the technology disclosed in this document, by using the core mainly made of an elastic material used for a spring, the rotation transmission performance toward the distal end side is improved.

Patent Documents 1 and 2 do not disclose the technology of the present invention in a point that the core inserted into the coil has a structure of a combined truncated cone to reduce a rotation angle of the proximal end side and to increase a torsional force of the distal end side so that the rotation transmission performance toward the distal end side and the perforation performance at the completely occluded lesion are improved. These performances are important technical problems to let the guide wire be inserted into the vascular lesion.

The present invention provides a guide wire capable of significantly improving passability at the vascular lesion.

In order to achieve the above and other objects, in the guide wire of the present invention, a distal end portion of the core, which has a portion gradually tapered in diameter from a proximal end side to a distal end side, is inserted into the outer coil. The distal end of the outer coil is connected with the distal end of the distal end portion of the core to form a distal joining section. The proximal end of the outer coil is connected with the proximal end of the distal end portion of the core to form an outer coil proximal joining section.

The distal end portion of the core is a combined truncated cone formed by longitudinally connecting at least two truncated cones. A longitudinal length of each of the truncated cones is reduced in order from the proximal end side to the distal end side. An outer diameter ratio between a maximum outer diameter of the proximal end and a minimum outer diameter of the distal end of each of the truncated cones is increased in order from the proximal end side to the distal end side. The outer diameter ratio is calculated by dividing the maximum outer diameter of the proximal end by the minimum outer diameter of the distal end.

When a maximum outer diameter of the combined truncated cone is defined as D0, a minimum outer diameter of the combined truncated cone is defined as D1, a total length of the combined truncated cone is defined as L, an outer diameter at an arbitrary position X, which is located from a center in a cross section of the maximum outer diameter D0 to the distal end of the combined truncated cone, is defined as Dm, and the arbitrary position X is within a range of 0<X<L, the outer diameter Dm of the combined truncated cone satisfies the following relational expression:

$$Dm > \{D0 - (D0 - D1)X/L\}.$$

The outer coil includes a large diameter proximal portion and a small diameter distal portion in order from the proximal end side to the distal end side. When an outer diameter of the large diameter proximal portion of the outer coil is defined as B1, an outer diameter of the small diameter distal portion of the outer coil is defined as B2, and a maximum outer diameter of the proximal end of the combined truncated cone located at the most distal end in the combined truncated cone is defined as D2, an outer diameter ratio (D2/D1) between the maximum outer diameter D2 of the proximal end and the minimum outer diameter D1 of the distal end in the combined truncated cone located at the most distal end in the combined truncated cone is greater than the outer diameter ratio (B1/B2) of the outer coil satisfying the following relational expression:

$$\{(D2/D1) > (B1/B2)\}.$$

The inner coil includes a large diameter proximal portion and a small diameter distal portion in order from the proximal end side to the distal end side. The inner coil is provided outside the distal end portion of the core and inside the outer coil. The inner coil has a shorter longitudinal length than the outer coil and is arranged concentrically with the outer coil. The distal end of the small diameter distal portion of the inner coil is connected with the distal end of the distal end portion of the core to form a distal joining section. The proximal end of the large diameter proximal portion of the inner coil is connected with the proximal end of the distal end portion of the core to form an inner coil proximal joining section.

The combined truncated cone is formed by a first truncated cone and a second truncated cone in order from the proximal end side to the distal end side. At least a part of the second truncated cone is arranged in the inner coil. When a maximum outer diameter of the proximal end of the second truncated cone is defined as D2, a minimum outer diameter of the distal end of the second truncated cone is defined as D1, an outer diameter of the large diameter proximal portion of the inner coil is defined as A1, and an outer diameter of the small diameter distal portion of the inner coil is defined as A2, an outer diameter ratio (D2/D1) of the second truncated cone is greater than an outer diameter ratio (D0/D2) of the first truncated cone satisfying the following relational expression:

$$\{(D2/D1) > (D0/D2)\}$$

and the outer diameter ratio (D2/D1) of the second truncated cone, the outer diameter ratio (A1/A2) of the inner coil and the outer diameter ratio (B1/B2) of the outer coil satisfy the following relational expression:

$$(D2/D1) > (A1/A2) > (B1/B2).$$

The outer coil and the inner coil include a large constant diameter proximal portion, a tapered middle portion and a small constant diameter distal portion in order from the proximal end side to the distal end side. The tapered middle portion of the outer coil and the tapered middle portion of the inner coil are arranged to be overlapped with each other.

The distal end of the small constant diameter distal portion of the outer coil, the distal end of the small constant diameter distal portion of the inner coil, and the distal end of the distal end portion of the core are connected with each other to form a distal joining section. The proximal end of the large constant diameter proximal portion of the outer coil is connected with the proximal end of the distal end portion of the core to form an outer coil proximal joining section. The proximal end of the large constant diameter proximal portion of the inner coil is connected with the distal end portion of the core to form an inner coil proximal joining section.

The large constant diameter proximal portion of the outer coil, the large constant diameter proximal portion of the inner coil, and the proximal end side (large diameter side) of the second truncated cone are integrally connected with each other to form a middle joining section.

The outer diameter ratio (D2/D1) of the truncated cone located at the most distal end in the combined truncated cone is 1.50 to 4.20. The outer diameter ratio (A1/A2) of the inner coil is 1.15 to 2.80. The outer diameter ratio (B1/B2) of the outer coil is 1.10 to 1.80.

In the guide wire of the present invention, the distal end portion of the core, which is inserted into the outer coil, is a combined truncated cone formed by longitudinally connecting at least two truncated cones. In addition, the longitudinal length of each of the truncated cones is reduced in order from the proximal end side to the distal end side. Furthermore, the outer diameter ratio between the maximum outer diameter of the proximal end and the minimum outer diameter of the distal end in each of the truncated cones is increased in order from the proximal end side to the distal end side, the outer diameter ratio being calculated by dividing the maximum outer diameter of the proximal end by the minimum outer diameter of the distal end.

By doing so, when rotation operation is performed to the guide wire from the proximal end side to the distal end side, the rotation angle of the proximal end side is reduced and the torsional moment applied to the distal end side is increased.

The outer diameters of the components of the combined truncated cone satisfy a predetermined relational expression.

By doing so, although the distal end portion of the core has a small diameter and a tapered shape, the outer diameter ratio of the truncated cone located at the most distal end can be greater than the outer diameter ratio of the truncated cone of the proximal end side.

Because of this, the rotation angle of the proximal side can be reduced and the torsional moment applied to the distal end side can be increased during the rotating operation. Thus, the perforation performance can be significantly improved at the occluded lesion.

The outer coil includes a large diameter proximal portion and a small diameter distal portion in order from the proximal end side to the distal end side. When the outer diameter of the large diameter proximal portion of the outer coil is defined as B1, the outer diameter of the small diameter distal portion of the outer coil is defined as B2, and the maximum outer diameter of the proximal end of the combined truncated cone located at the most distal end in the combined truncated cone is defined as D2, the outer diameter ratio (D2/D1) between the maximum outer diameter D2 of the proximal end and the minimum outer diameter D1 of the distal end in the truncated cone located at the most distal end in the combined truncated cone is greater than the outer diameter ratio (B1/B2) of the outer coil satisfying the following relational expression:

$$\{(D2/D1) > (B1/B2)\}.$$

By doing so, the torsional force, which is reduced by reducing the diameter of the distal end portion of the core inserted into the outer coil, is compensated by the tapered shape of the outer coil. Thus, even if the diameter of the distal end portion of the core is small, the outer diameter ratio of the truncated cone located at the most distal end is increased. Because of this, the torsional moment applied to the distal end side is increased. As explained above, when the outer coil having the tapered shape is simultaneously used, the rotation transmission performance toward the distal end side can be further improved.

The outer coil and the inner coil include a large diameter proximal portion and a small diameter distal portion in order from the proximal end side to the distal end side. The inner coil is provided outside the distal end portion of the core and inside the outer coil. The inner coil has a shorter longitudinal length than the outer coil. The inner coil is arranged concentrically with the outer coil. The distal end of the small diameter distal portion of the inner coil, the distal end of the distal end portion of the core, and the distal end of the small diameter distal portion of the outer coil are connected with each other to form a distal joining section. The proximal end of the large diameter proximal portion of the inner coil is connected with the distal end portion of the core to form an inner coil proximal joining section.

The combined truncated cone is formed by a first truncated cone and a second truncated cone in order from the proximal end side to the distal end side. At least a part of the second truncated cone is arranged in the inner coil. when the maximum outer diameter of the proximal end of the second truncated cone is defined as D2, the minimum outer diameter of the distal end is defined as D1, an outer diameter of the large diameter proximal portion of the inner coil is defined as A1, and an outer diameter of the small diameter distal portion of the inner coil is defined as A2, an outer diameter ratio (D2/D1) of the second truncated cone is greater than an outer diameter ratio (D0/D2) of the first truncated cone satisfying the following relation:

{(D2/D1)>(D0/D2)} and the outer diameter ratio (D2/D1) of the second truncated cone, the outer diameter ratio (A1/A2) of the inner coil and the outer diameter ratio (B1/B2) of the outer coil satisfy the following relational expression:

(D2/D1)>(A1/A2)>(B1/B2).

By doing so, both the inner coil and the outer coil have a tapered shape and the outer diameter ratio of the inner coil is greater than that of the outer coil to further compensate the torsional force, which is reduced by reducing the diameter of the distal end portion of the core inserted into the inner coil. Thus, even if the diameter of the distal end portion of the core is small, the outer diameter ratio of the truncated cone located at the most distal end becomes the largest. Therefore, the torsional moment applied to the distal end side is increased. As explained above, when the outer coil and the inner coil both having the tapered shape are simultaneously used, the rotation transmission performance toward the distal end side can be further improved.

Because of this, the rotation angle of the proximal side is further reduced, the bending rigidity and the buckling strength of the combined truncated cone are improved at the distal end portion of the core, and the torsional moment toward the distal end side is increased. Thus, the perforation performance can be significantly improved at the completely occluded lesion.

The outer coil and the inner coil include a large constant diameter proximal portion, a tapered middle portion and a small constant diameter distal portion in order from the proximal end side to the distal end side. The tapered middle portion of the outer coil and the tapered middle portion of the inner coil are arranged to be overlapped with each other.

By doing so, the outer coil and the inner coil are coaxial and have approximately same tapered shape at the tapered middle portion, which is the position overlapped with each other. Therefore, the rotation can be easily transmitted from the proximal end side (large diameter side) to the distal end side (small diameter side) by both coils.

The distal end of the small constant diameter distal portion of the outer coil, the distal end of the small constant diameter distal portion of the inner coil, and the distal end of the distal end portion of the core are connected with each other to form the distal joining section. The proximal end of the large constant diameter proximal portion of the outer coil is connected with the proximal end of the distal end portion of the core to form the outer coil proximal joining section. The proximal end of the large constant diameter proximal portion of the inner coil is connected with the distal end portion of the core to form the inner coil proximal joining section. The large constant diameter proximal portion of the outer coil, the large constant diameter proximal portion of the inner coil and the proximal end side of the second truncated cone are integrally connected with each other to form a middle joining section.

By doing so, the middle joining section is formed by integrally connecting the outer coil, the inner coil and the second truncated cone at the maximum diameter side. Thus, the rotating force is integrally transmitted to the distal end side. Because of this, the rotation transmission performance toward the distal end side (small diameter side) can be further improved.

The outer diameter ratio (D2/D1) of the truncated cone located at the most distal end in the combined truncated cone is 1.50 to 4.20. The outer diameter ratio (A1/A2) of the inner coil is 1.15 to 2.80. The outer diameter ratio (B1/B2) of the outer coil is 1.10 to 1.80. The outer diameter ratio (D2/D1) of the truncated cone located at the most distal end is greater than the outer diameter ratio (A1/A2) of the inner coil. The outer diameter ratio (A1/A2) of the inner coil is greater than the outer diameter ratio (B1/B2) of the outer coil.

If the ratios are less than the above described ranges, the rotation angle of the proximal side is increased when the rotating operation is performed from the proximal end side to the distal end side. In such a case, the torsional moment toward the distal end side is reduced and it becomes difficult to let the guide wire be inserted into the stenotic portion and the completely occluded lesion. If the ratios are more than the above described ranges, although the rotation angle of the proximal side is reduced, the torsional moment becomes large. In particular, torsional resistance of the small-diameter core connected with the inner coil and torsional residence of a coil wire of the small-diameter inner coil itself become insufficient. In such a case, the coil is not durable against high torsional moment and the coil starts to meander. This deteriorates the rotation transmission performance toward the distal end side.

In addition, a body part (e.g. cardiovascular and lower extremity vessels) to be treated, an inner vascular diameter, and practical dimensions of a medical tool (e.g. guiding catheter, balloon catheter and micro catheter) used for the radial dilation treatment are considered.

DETAILED DESCRIPTION OF THE INVENTION

Hereafter, the guide wire of an embodiment of the present invention will be explained.

Figure 1:
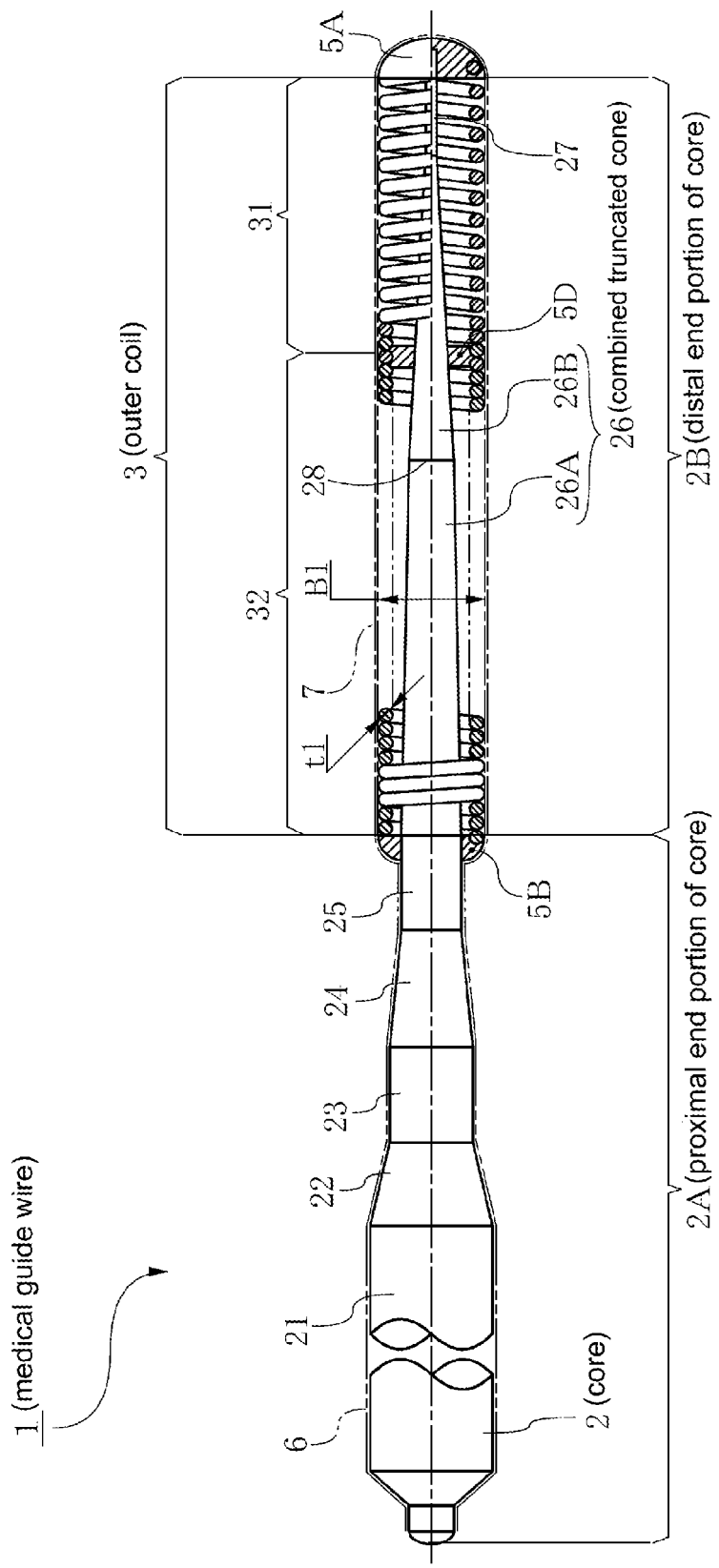
FIG. 1 is a side view showing a partially cutaway guide wire according to a first embodiment of the present invention.
Figure 2:
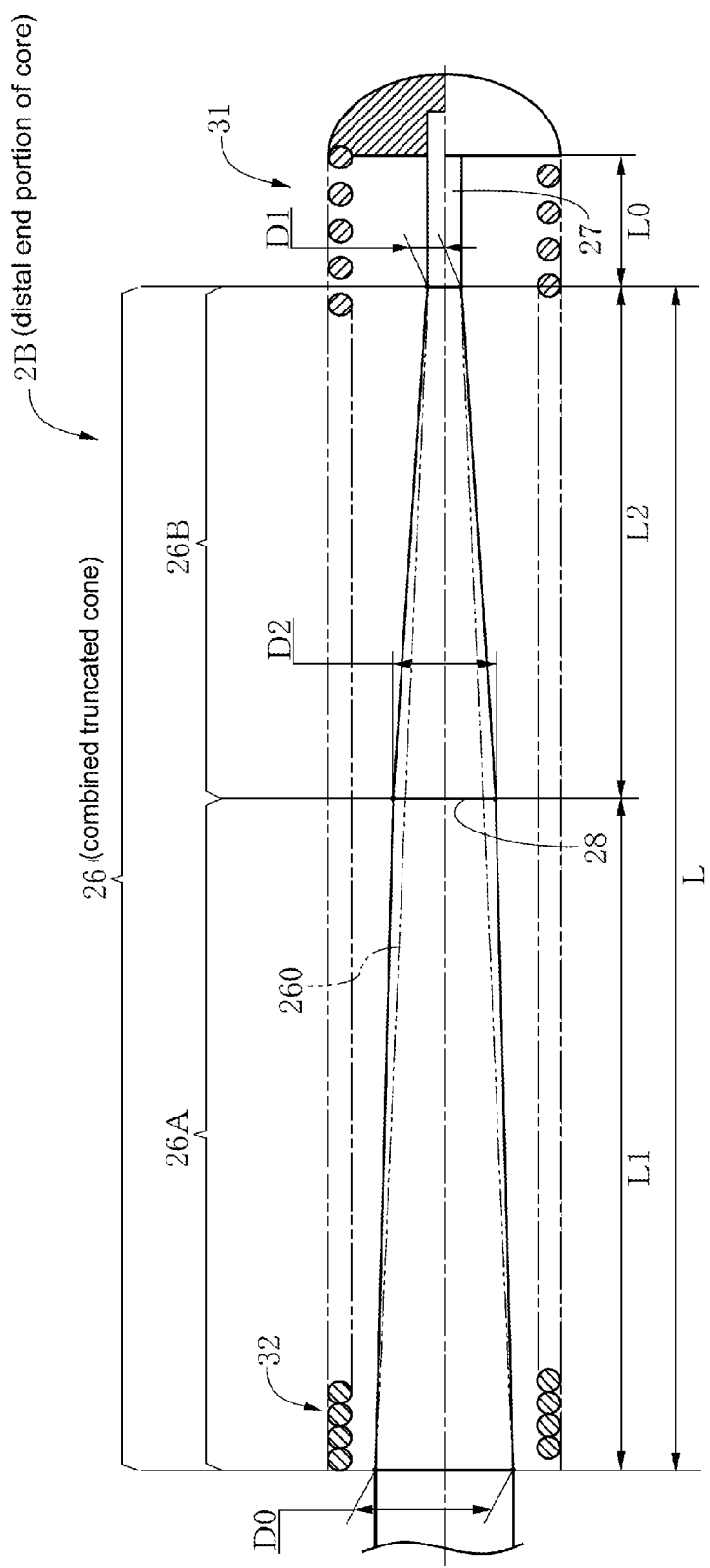
FIG. 2 is a side view showing a partially cutaway distal end portion of the guide wire having a combined truncated cone formed by combining two truncated cones.

FIG. 1 shows an overall view of a guide wire 1 of a first embodiment of the present invention. FIG. 2 shows a main part of the distal end portion. The guide wire 1 includes a core 2, an outer coil 3, a fluorocarbon polymer coating 6, and a hydrophilic polymer coating 7. The core 2 includes a proximal end portion 2A of the core and a distal end portion 2B of the core. The core 2 includes a portion gradually tapered in diameter from the proximal end side to the distal end side.

The distal end portion 2B of the core is inserted into the outer coil 3. By using a bonding member, the distal end of the outer coil 3 and the distal end of the distal end portion 2B of the core are connected with each other to form a distal joining section 5A having a rounded shape at the tip, and the proximal end of the outer coil 3 and the proximal end of the distal end portion 2B of the core are connected with each other to form an outer coil proximal joining section 5B. The fluorocarbon polymer coating 6 is formed on an outer periphery of the proximal end portion 2A of the core located at the proximal end side (large diameter side). The hydrophilic polymer coating 7 is formed on an outer periphery of the outer coil 3. Note that the guide wire 1 of the present invention has an extremely small diameter relative to its length. Therefore, the guide wire 1 is partially exaggerated or omitted in drawings because it is difficult to illustrate the guide wire 1 in a specified area if the same scaling is used for horizontal and vertical directions.

The outer diameter of the core 2 is gradually reduced from the proximal end side to the distal end side in the following order: a first constant diameter portion 21, a first tapered portion 22, a second constant diameter portion 23, a second tapered portion 24, a third constant diameter portion 25, a combined truncated cone 26 formed by combining a first truncated cone 26A and a second truncated cone 26B, and a fourth constant diameter portion 27. The outer diameter is gradually reduced from 0.3556 mm (0.014 inch: for the cardiovascular treatment) to 0.060 mm.

The outer diameter of the combined truncated cone 26 is gradually reduced from 0.180 mm at the proximal end (large diameter side) to 0.060 mm at the distal end (small diameter side). The outer coil proximal joining section 5B of the outer coil 3 is connected with the proximal end (large diameter side) of the first truncated cone 26A by using a brazing material or other means.

The core 2 is made from a stainless steel wire, a Ni—Ti alloy wire or the like. For example, as shown in Japanese Patent Laid-Open Publication No. 2002-69586, the stainless steel wire having high strength manufactured by repeating a wire drawing process and an annealing process is used. In addition, as shown in Japanese Patent Laid-Open Publication No. 2002-69555, a Ni—Ti alloy wire manufactured by thermal processing under certain conditions is used. An austenitic stainless steel wire having a tensile strength of 2200 MPa to 3500 MPa is preferably used.

This is because the tensile strength can be easily increased by a treatment of diameter reduction and wire drawing. In addition, a process of centerless grinding of the combined truncated cone 26 becomes easier although it will be described later. Note that the combined truncated cone 26 here means a structure of having a plurality of truncated cone shapes in the longitudinal direction manufactured by grinding a single wire. The core 2 can be formed by welding and joining different kinds of wires between the distal end portion 2B and the proximal end portion 2A. For example, same as the combination of the material of the core, the proximal end portion 2A can be the stainless steel wire and the distal end portion 2B can be the Ni—Ti alloy wire.

The outer coil 3 is formed by winding one or a plurality of wires. The outer coil 3 has a constant outer diameter B1 of 0.330 mm and a longitudinal length of 160 mm. A wire diameter t1 of the coil wire is 0.060 mm. A first outer coil 31 located at the distal end side is made of a coil formed by winding a radiopaque wire including gold, platinum, nickel-containing gold or nickel-containing platinum, for example. The longitudinal length of the first outer coil 31 is 40 mm. The first outer coil 31 is roughly wound so that a distance between windings is 1.20 times to 1.90 times greater than the wire diameter t1. Alternatively, 40 mm of the longitudinal length can be divided into 20 mm of densely wound part located at the proximal end side and 20 mm of roughly wound part located at the distal end side. A second outer coil 32 located at the proximal end side is made of a radiolucent stainless steel wire. The longitudinal length of the second outer coil 32 is 120 mm. The second outer coil 32 is densely wound.

The first outer coil 31 and the second outer coil 32 are connected with each other at a middle joining section 5D by screw fitting of the coil wires and fixed by using a brazing material or other means. Instead of the screw fitting, the coil wires can be connected with each other by welding, for example. Note that an austenitic stainless steel wire having a tensile strength of 2200 MPa to 3500 MPa is preferably used for the material of the coil wire of the second outer coil 32. By doing so, the coil wire having the tensile strength is obtained and the coil wire can be densely wound. Thus, the fatigue resistance can be increased by high torsional stress and high initial tension.

The outer coil 3 can be formed by using one or a plurality of radiopaque wires including gold, platinum, nickel-containing gold or nickel-containing platinum, for example, and the proximal end side can be densely wound within the range between ¾ and ⅞ in the total length, while the rest part of the distal end side is roughly wound.

Figure 3:
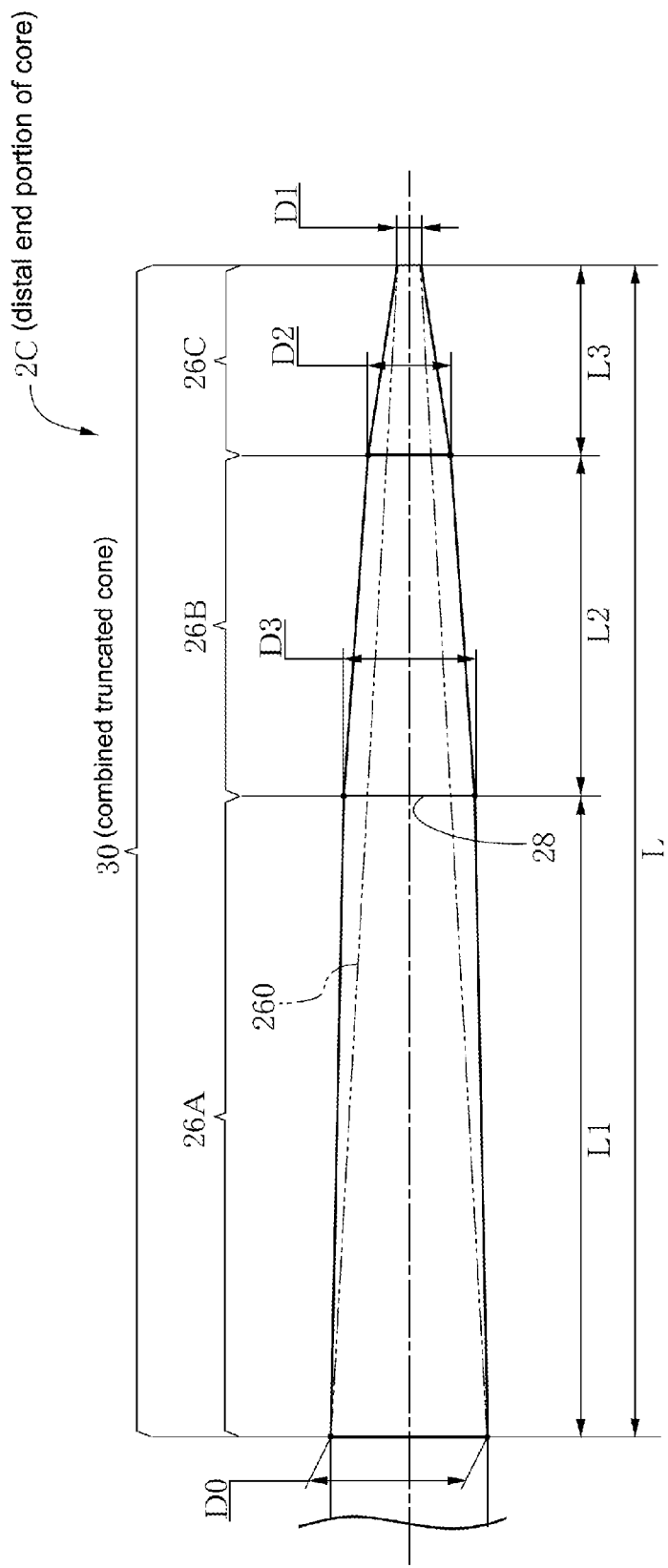
FIG. 3 is a side view showing a combined truncated cone formed by combining three truncated cones according to a second embodiment.

FIGS. 2 and 3 respectively show different shapes of the distal end portions 2B, 2C. FIG. 2 shows the distal end portion 2B of the core having the combined truncated cone 26 formed by combining two truncated cones according to the first embodiment. FIG. 3 shows the distal end portion 2C of the core formed by three truncated cones according to the second embodiment. Except for the distal end portion 2C of the core, other specifications of the second embodiment are same as the first embodiment. Therefore, the same reference numerals are used for the same components.

In FIG. 2, the distal end portion 2B of the core is formed by the combined truncated cone 26 and the fourth constant diameter portion 27 in order from the proximal end side to the distal end side. The combined truncated cone 26 is formed by two truncated cones: one is the first truncated cone 26A and the other is the second truncated cone 26B. In the first truncated cone 26A, the longitudinal length L1 is 100 mm, the maximum outer diameter (the maximum outer diameter of the combined truncated cone 26) D0 is 0.180 mm, and the minimum outer diameter D2 is 0.125 mm. In the second truncated cone 26B, the longitudinal length L2 is 50 mm, the maximum outer diameter D2 of the second truncated cone 26B is 0.125 mm, and the minimum outer diameter (the minimum outer diameter of the combined truncated cone 26) D1 is 0.060 mm. In the fourth constant diameter portion 27, the longitudinal length L0 is 10 mm and the outer diameter is 0.060 mm. Note that the fourth constant diameter portion 27 is not necessarily provided on the distal end portion 2B of the core. When flexibility and bending deformation of the most distal end are emphasized, the fourth constant diameter portion 27 should be prepared preferably. When the perforation performance of the most distal end is emphasized, the fourth constant diameter portion 27 is preferably not provided. Each of the options can be selected according to symptom of the lesion.

The longitudinal length L1 of the first truncated cone 26A is 100 mm, the longitudinal length L2 of the second truncated cone 26B is 50 mm, thus the longitudinal length is reduced from the proximal end side to the distal end side (L1>L2). The outer diameter ratio D0/D2 of the first truncated cone 26A is 1.44, the outer diameter ratio D2/D1 of the second truncated cone 26B is approximately 2.08, thus the outer diameter ratio is increased from the proximal end side to the distal end side {(D0/D2)<(D2/D1)}.

In FIG. 3, the distal end portion 2C of the core is formed by continuously combining the first to third truncated cones 26A, 26B and 26C to form a combined truncated cone 30. In the first truncated cone 26A, the longitudinal length from the proximal end side to the distal end side is L1 (mm), the maximum outer diameter is D0 (mm), and the minimum outer diameter is D3 (mm). In the second truncated cone 26B, the longitudinal length is L2 (mm), the maximum outer diameter is D3 (mm), and the minimum outer diameter is D2 (mm). In a third truncated cone 26C, the longitudinal length is L3 (mm), the maximum outer diameter is D2 (mm), and the minimum outer diameter is D1 (mm). Note that the fourth constant diameter portion 27 shown in FIG. 2 is not provided.

The longitudinal length L1, L2, L3 of each of the truncated cones 26A, 26B and 26C of the combined truncated cone 30 is reduced in order from the proximal end side to the distal end side (L1>L2>L3). The outer diameter ratio (D0/D3), (D3/D2), (D2/D1) of each of the truncated cones 26A, 26B and 26C are increased in order from the proximal end side to the distal end side {(D0/D3)<(D3/D2)<(D2/D1)}.

As explained above, in the present invention, the distal end portions 2B, 2C of the core are the combined truncated cones 26, 30 formed by longitudinally connecting at least two truncated cones. The longitudinal length of each of the truncated cones is reduced in order from the proximal end side to the distal end side, i.e., from the first truncated cone 26A to the second truncated cone 26B, and further to the third truncated cone 26C. The outer diameter ratio between the maximum outer diameter of the proximal end and the minimum outer diameter of the distal end in each of the truncated cone is increased in order from the proximal end side to the distal end side. The outer diameter ratio is calculated by dividing the maximum outer diameter of the proximal end by the minimum outer diameter of the distal end.

By doing so, the rotation angle of the proximal end side is reduced and the torsional moment toward the distal end side is increased. Thus, the perforation performance at the stenotic portion and the completely occluded lesion can be improved because of high rotation transmission performance applied to the distal end side.

More specifically, when the rotation angle of the distal end is same, the rotation angle of the proximal end side can be reduced. This is because the rotation angle of the proximal end side, i.e., torsion angle, is reduced as the torsional rigidity increases, the torsional rigidity can be expressed by the product of a transverse elasticity modulus and a sectional secondary moment, and the sectional secondary moment is higher in the structure of the combined truncated cones 26, 30 than the structure of a virtual single truncated cone 260 shown by two-dot chain lines in FIGS. 2 and 3.

When the proximal end side is pushed and pulled, the bending rigidity and the buckling strength of the distal end can be increased. This is because the bending rigidity can be expressed by the product of a longitudinal elastic modulus and the sectional secondary moment, and the sectional secondary moment is higher in the structure of the combined truncated cones 26, 30 than the structure of the single truncated cone 260.

Since a compression stress is inversely proportional to a cross-sectional area, the compression stress is reduced as the cross-sectional area increases. In particular, in the combined truncated cones 26, 30, a joint portion 28, which is a portion from which the outer diameter of the core is significantly changed compared to the other portions, has a larger cross-sectional area than the corresponding area in the single truncated cone 260, and therefore the compression stress becomes low.

Therefore, when the guide wire is pushed and pulled in the longitudinal direction, because of the existence of the joint portion 28 having a larger cross-sectional area, the buckling strength can be increased in the structure of the combined truncated cones 26, 30 than the structure of the single truncated cone 260.

Figure 4:
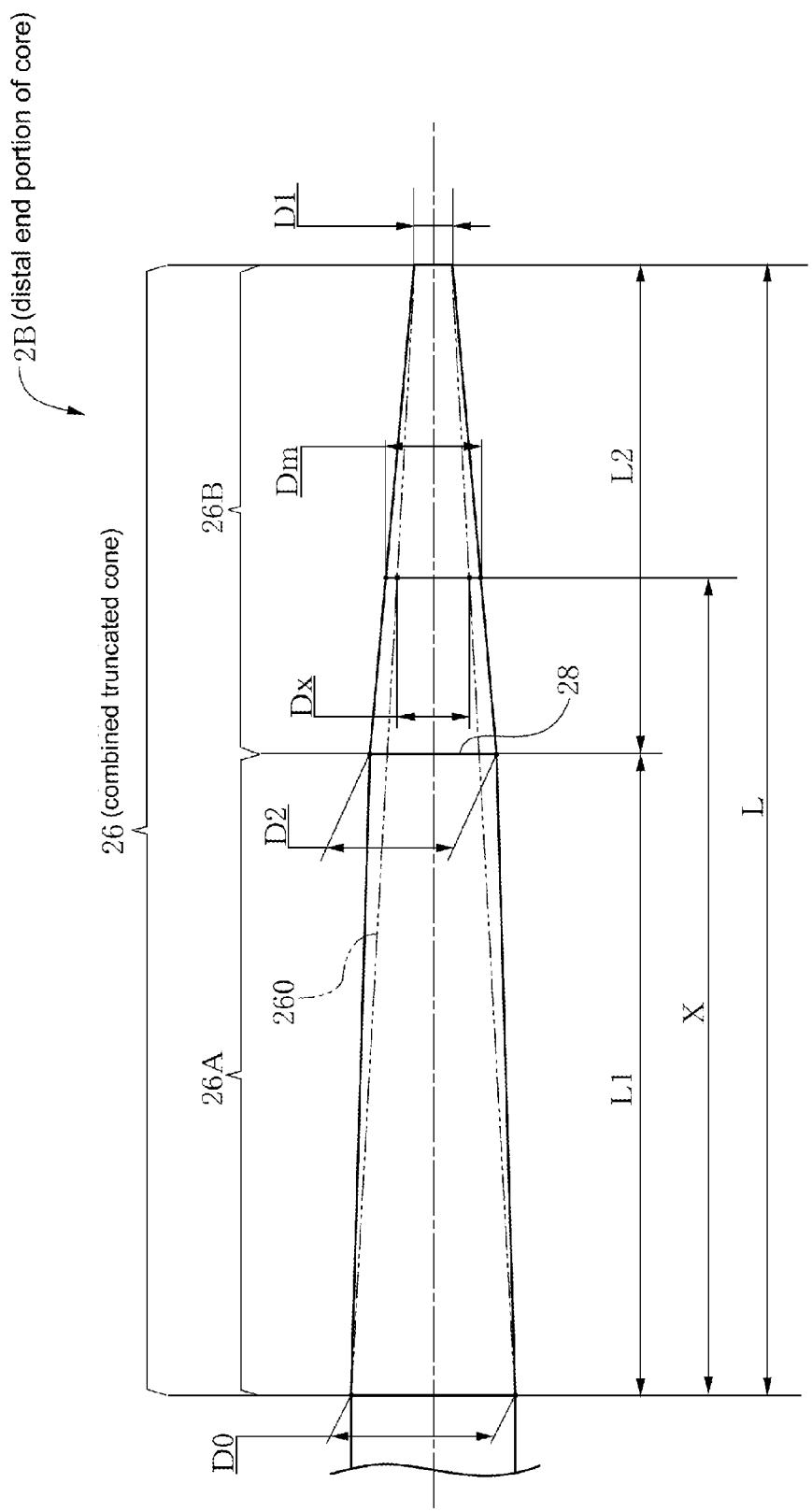
FIG. 4 is an explanation drawing showing a relational expression between an outer diameter ratio of the combined truncated cone formed by combining two truncated cones and an outer diameter of a virtual single truncated cone.

FIG. 4 is an explanation drawing showing a relational expression between the outer diameter of the combined truncated cone 26 of the distal end portion 2B of the core of the present invention and the outer diameter of the virtual single truncated cone 260.

Solid lines indicate the combined truncated cone 26 formed by two truncated cones of the first embodiment of the present invention. Two-dot chain lines indicate the virtual single truncated cone 260 to explain the relation. Note that the fourth constant diameter portion 27 is omitted.

In the combined truncated cone 26, the maximum outer diameter is D0 (mm), the minimum outer diameter is D1 (mm), and the total length is L (mm). When an arbitrary position of the combined truncated cone 26 is defined as X (mm), the arbitrary position X (mm) which is located from a center in a cross section of the maximum outer diameter D0 (mm) to the distal end, the arbitrary position X (mm) is more than 0 mm and less than L mm (0<X<L), the outer diameter at the arbitrary position X (mm) is defined as Dm (mm), and the outer diameter of the virtual single truncated cone 260 is defined as Dx (mm), the outer diameter Dx (mm) satisfies the following relational expression (1):

$$Dx = D0 - (D0 - d1)X/L \qquad (1).$$

Since the outer diameter Dm (mm) of the combined truncated cone 26 is larger at the arbitrary position X (mm) than the outer diameter Dx (mm) (Dm>Dx), the following relational expression (2) is satisfied:

$$Dm > \{D0 - (D0 - D1)X/L\} \qquad (2).$$

The present invention is characterized in that the distal end portions 2B, 2C of the core satisfy the above described relational expression (2). By doing so, the rotation angle of the proximal end side is reduced and the bending rigidity and the buckling strength of the distal end is increased. Thus, the torsional moment of the distal end is increased. As a result, the structure of the distal end portions 2B, 2C of the core capable of improving the perforation performance and the fatigue resistance at the lesion can be obtained.

Figure 5:
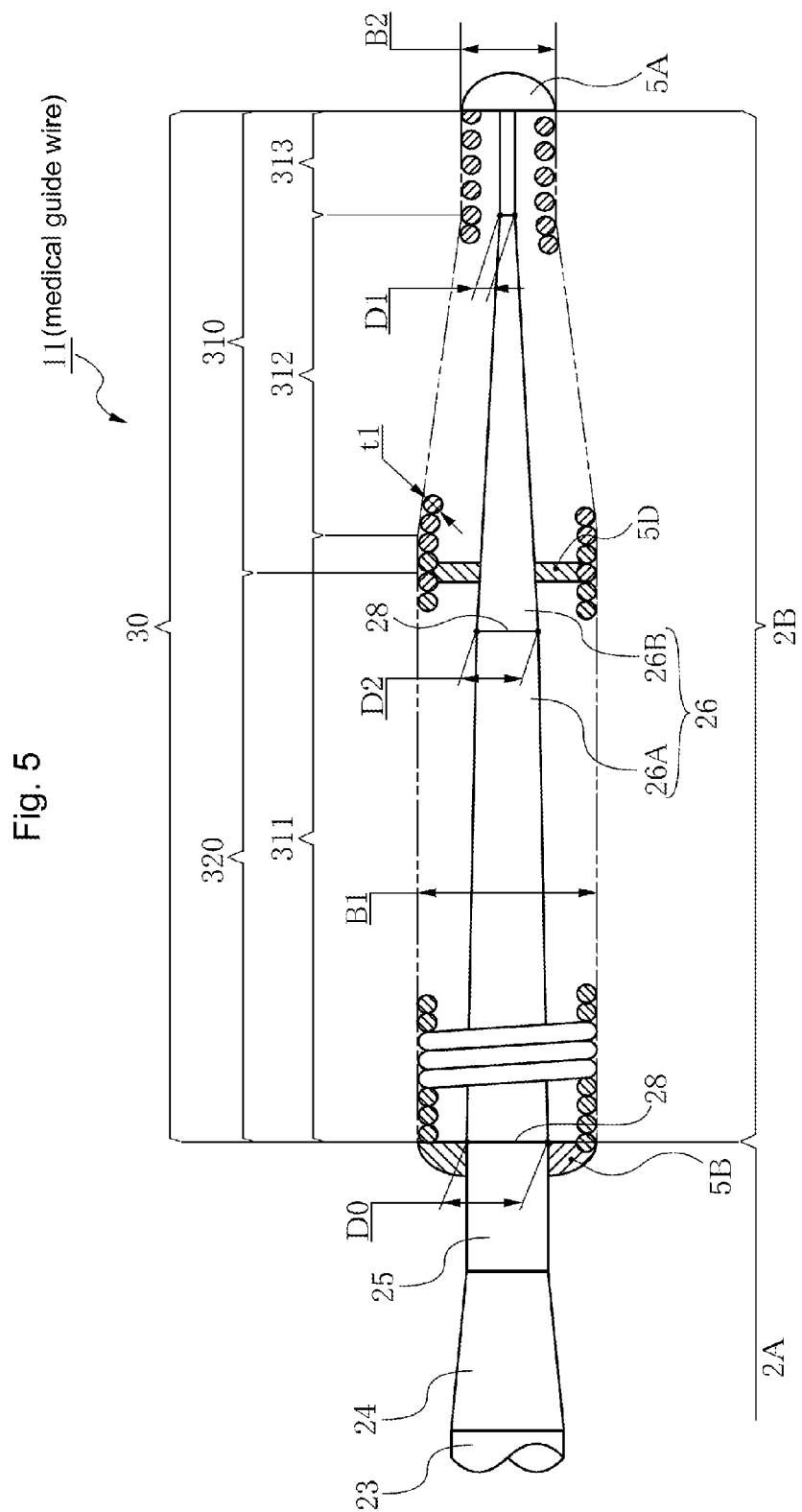
FIG. 5 is a side view showing a partially cutaway distal end portion of the guide wire according to a third embodiment.

FIG. 5 shows a guide wire 11 of the third embodiment. The guide wire 11 is different from the guide wire 1 of the first embodiment in a point that an outer coil 30 is formed as a tapered shape from the proximal end side to the distal end side. Note that the fluorocarbon polymer coating 6 and the hydrophilic polymer coating 7 are omitted in the drawing.

In the outer coil 30, the outer diameter B1 of a large constant diameter proximal portion (large diameter proximal portion) 311 is 0.330 mm, the longitudinal length is 125 mm, the outer diameter of a tapered middle portion 312 is gradually reduced from 0.330 mm to 0.260 mm, the longitudinal length is 20 mm, the outer diameter B2 of a small constant diameter distal portion (small diameter distal portion) 313 is 0.260 mm, and the longitudinal length is 15 mm. The wire diameter t1 and the material of the coil wire are same as the first embodiment. The second outer coil 320 is made of a radiolucent wire and the first outer coil 310 is made of a radiopaque wire. The large constant diameter proximal portion (large diameter proximal portion) 311 and the tapered middle portion 312 of the outer coil 30 are densely wound. Same as the first outer coil 31 of the outer coil 3 of the first embodiment, the small constant diameter distal portion (small diameter distal portion) 313 is a coil roughly wound. Note that the small constant diameter distal portion (small diameter distal portion) 313 can be formed so that the proximal end side is densely wound and the distal end side is roughly wound.

When considering the outer diameter 0.3556 mm (0.0014 inch) of the guide wire used for the cardiovascular treatment, the outer diameter ratio B1/B2 between the outer diameter B1 of the large constant diameter proximal portion (large diameter proximal portion) 311 of the outer coil 30 and the outer diameter B2 of the small constant diameter distal portion (small diameter distal portion) 313 is 1.10 to 1.50. When considering the maximum outer diameter 0.4572 mm (0.018 inch) of the guide wire used for the lower extremity vessels, the outer diameter ratio B1/B2 is 1.10 to 1.80.

When considering both for the cardiovascular treatment and the lower extremity vessels, the outer diameter ratio B1/B2 is 1.10 to 1.80, and preferably 1.15 to 1.80. The outer diameter ratio B1/B2 of the outer coil 30 of the third embodiment is approximately 1.27.

The outer diameter ratio (D2/D1) between the maximum outer diameter D2 of the proximal end and the minimum outer diameter D1 of the distal end in the second truncated cone 26B located at the most distal end in the combined truncated cone 26 is greater than the outer diameter ratio (B1/B2) of the outer coil 30 {(D2/D1)>(B1/B2)}. In the third embodiment, the outer diameter ratio B1/B2 of the outer coil 30 is approximately 1.27 and the outer diameter ratio D2/D1 of the second truncated cone 26B located at the most distal end is approximately 2.08. Therefore, the outer diameter ratio D2/D1 of the second truncated cone 26B located at the most distal end is greater than the outer diameter ratio B1/B2 of the outer coil {(D2/D1)>(B1/B2)}. By doing so, the torsional force, which is reduced by reducing the diameter of the distal end portion 2B of the core inserted into the outer coil 30, can be compensated by the outer coil 30 tapered toward the distal end side. Even if the diameter of the distal end portion 2B of the core is small, when the outer diameter ratio D2/D1 between the proximal end and the distal end of the second truncated cone 26B located at the most distal end is increased, the torsional moment toward the distal end side is increased. Thus, when the outer coil 30 having a tapered shape is simultaneously used, the rotation transmission performance toward the distal end side can be further improved.

In addition, even if the diameter of the distal end portion 2B of the core is small, when the outer diameter ratio D2/D1 between the proximal end and the distal end of the second truncated cone 26B located at the most distal end is increased to the maximum extent, the torsional moment toward the distal end side is increased. Thus, when the outer coil 30 having a tapered shape is simultaneously used, the rotation transmission performance toward the distal end side can be further improved.

Figure 6:
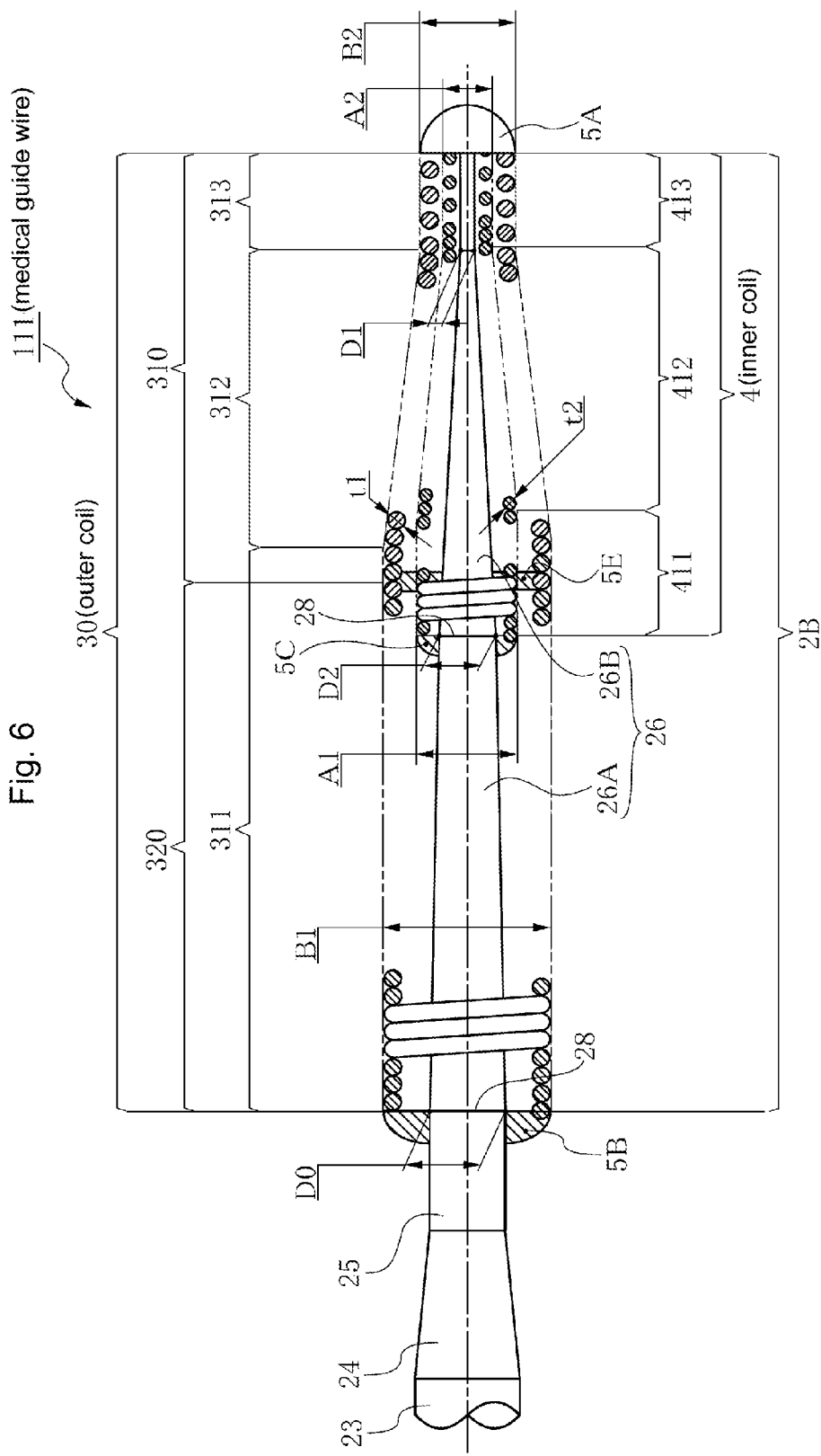
FIG. 6 is a side view showing a partially cutaway distal end portion of the guide wire according to a fourth embodiment.

FIG. 6 shows a guide wire 111 of the fourth embodiment. The guide wire 111 is different from the guide wire 11 of the third embodiment in a point that an inner coil 4 is provided inside the outer coil 30. The inner coil 4 has a smaller longitudinal length than the outer coil 30. The inner coil 4 is arranged concentrically with the outer coil 30. The inner coil has a tapered shape from the proximal end side to the distal end side. Note that the fluorocarbon polymer coating 6 and the hydrophilic polymer coating 7 are omitted in the drawing. The distal end portion 2B of the core is inserted into the inner coil 4 and connected with the distal end of the outer coil 30 and the distal end of the distal end portion 2B of the core using a bonding member or the like to form the distal joining section 5A having a rounded shape at the tip. The proximal end of the inner coil 4 is connected with the proximal end of the distal end portion 2B of the core to form an inner coil proximal joining section 5C. In a middle joining section 5E, the inner coil 4, the outer coil 30 and the distal end portion 2B of the core are integrally connected with each other. Note that the middle joining section 5E can be formed by connecting the inner coil 4 with the distal end portion 2B of the core or connecting the inner coil 4 with the outer coil 3.

In the inner coil 4, the outer diameter A1 of a large constant diameter proximal portion (large diameter proximal portion) 411 is 0.185 mm, the longitudinal length is 20 mm, the outer diameter of a tapered middle portion 412 is gradually reduced from 0.185 mm at the proximal end side to 0.130 mm at the distal end side, and the longitudinal length is 20 mm. The outer diameter A2 of a small constant diameter distal portion (small diameter distal portion) 413 is 0.130 mm, the longitudinal length is 15 mm, and the wire diameter t2 of the coil wire is 0.030 mm. The inner coil 4 is formed by using one or a plurality of wires to form the large constant diameter proximal portion (large diameter proximal portion) 411, the tapered middle portion 412, and the small constant diameter distal portion (small diameter distal portion 413). In the above described structure, the large constant diameter proximal portion and the tapered middle portion 412 are densely wound, while the small constant diameter distal portion 413 is roughly wound or divided into two parts: one is the densely wound part located at the proximal end side and the other is the roughly wound part located at the distal end side, same as the distal end side of the first outer coil of the above described third embodiment.

The coil wire of the inner coil 4 can be made of a radiopaque material same as the coil wire of the above described first outer coil 31. When using the radiopaque material, an alloy made of Pt and Ni containing 90 wt. % to 96 wt. % Pt and the balance Ni is preferably used. Ni component is contained because the longitudinal elastic modulus can be increased compared to the case of using only Pt. More preferably, a radiolucent stainless steel wire is used. In such a case, same as the second outer coil 32, an austenitic stainless steel wire having a tensile strength of 2200 MPa to 3500 MPa is more preferred. By doing so, the longitudinal elastic modulus becomes higher than the alloy made of Pt and Ni.

When considering the outer diameter 0.3556 mm (0.0014 inch) of the guide wire used for the cardiovascular treatment, the outer diameter ratio A1/A2 between the outer diameter A1 of the large constant diameter proximal portion (large diameter proximal portion) 411 of the inner coil 4 and the outer diameter A2 of the small constant diameter distal portion (small diameter distal portion) 413 is 1.15 to 1.70. When considering the maximum outer diameter 0.4572 mm (0.018 inch) of the guide wire used for the lower extremity vessels, the outer diameter ratio A1/A2 is 1.15 to 2.80.

When considering both for the cardiovascular treatment and the lower extremity vessels, the outer diameter ratio A1/A2 is 1.15 to 2.80, preferably 1.15 to 2.75, and more preferably 1.25 to 2.75. The outer diameter ratio A1/A2 of the inner coil 4 of the fourth embodiment is approximately 1.42.

The outer diameter ratio (D2/D1) between the maximum outer diameter D2 of the proximal end and the minimum outer diameter D1 of the distal end in the second truncated cone 26B located at the most distal end in the combined truncated cone 26 is greater than the outer diameter ratio D0/D2 of the first truncated cone 26A {(D2/D1)>(D0/D2)}. In addition, the outer diameter ratio D2/D1 of the second truncated cone 26B, the outer diameter ratio A1/A2 of the inner coil, and the outer diameter ratio B1/B2 of the outer coil satisfy the following relational expression (3):

$$(D2/D1) > (A1/A2) > (B1/B2) \quad (3).$$

In the fourth embodiment, the outer diameter ratio D2/D1 of the second truncated cone 26B is approximately 2.08 and the outer diameter ratio D0/D2 of the first truncated cone 26A is 1.44. Therefore, the outer diameter ratio D2/D1 of the second truncated cone 26B is greater than the outer diameter ratio D0/D2 of the first truncated cone 26A (approximately 2.08>1.44). In addition, the outer diameter ratio A1/A2 of the inner coil 4 is approximately 1.42 and the outer diameter ratio B1/B2 of the outer coil 30 is approximately 1.27. Therefore, the outer diameter ratio D2/D1 of the second truncated cone, the outer diameter ratio A1/A2 of the inner coil 4, and the outer diameter ratio B1/B2 of the outer coil 30 are respectively approximately 2.08>approximately 1.42>approximately 1.27. Thus, the following relational expression (3) is satisfied:

$$(D2/D1) > (A1/A2) > (B1/B2) \quad (3).$$

By satisfying the relational expression (3), the inner coil 4 is tapered toward the distal end side. Thus, when the outer coil 30 and the inner coil both having the tapered shape are simultaneously used, the torsional force, which is reduced by reducing the diameter of the second truncated cone 26B of the distal end portion 2B of the core inserted into the inner coil 4, can be further compensated.

Even if the diameter of the second truncated cone 26B is small, when the outer diameter ratio D2/D1 between the proximal end and the distal end of the second truncated cone 26B is increased to the maximum extent, the torsional moment to the distal end side is increased. Thus, when the inner coil 4 and the outer coil 30 both having a tapered shape are simultaneously used, the rotation transmission performance toward the distal end side can be further increased.

By doing so, the rotation angle of the proximal side of the core is reduced. In addition, the bending rigidity and the buckling strength of the distal end of the combined truncated cone 26 of the distal end portion 2B of the core is increased. Thus, the torsional moment toward the distal end side is increased and the perforation performance of the completely occluded lesion can be significantly increased.

The middle joining section 5E is preferably formed with a width of 0.22 mm to 1.5 mm by integrally connecting the proximal end side of the second truncated cone 26B, which is the large diameter side having a length of equal to or less than a half of the total length of the second truncated cone 26B, the large diameter side of the inner coil 4, which is the large diameter side having a length of equal to or less than a half of the total length of the inner coil 4, and the large diameter side of the outer coil 30 by using a bonding member such a brazing material.

It is preferred that the inner coil 4 and the outer coil 30 are densely wound at least from the proximal end to the middle joining section 5E. By doing so, when the proximal side of the core 2 is rotated, the rotation is transferred toward the distal end side via the coil by the following mechanism. The rotation force of the proximal side of the core 2 is transferred to the outer coil 30 having a larger outer diameter via the outer coil proximal joining section 5B, and then transferred to the integrally connected inner coil 4 and the second truncated cone 26B of the proximal end side both having a larger diameter via the middle joining section 5E.

As explained above, the rotation transmission force toward the distal end side is proportional to the outer diameter ratio between the large diameter proximal portion and the small diameter distal portion, the outer diameter ratio being calculated by dividing the outer diameter of the large diameter proximal portion by the outer diameter of the small diameter distal portion. If the middle joining section 5E is provided formed by integrally connecting the outer coil 30 located at the large diameter side, the inner coil 4 located at the large diameter side, and the second truncated cone 26B located at the proximal end side, the rotating force integrated by the tapered shape of the outer coil 30, the inner coil 4 and the second truncated cone 26B is transmitted to the distal end side. Thus, the rotation transmission performance toward the distal end side can be further increased.

Therefore, the middle joining section 5E is preferred to be provided by integrally connecting the densely wound large constant diameter proximal portion (large diameter proximal portion) 311 of the second outer coil 320 of the outer coil 30, the densely wound large constant diameter proximal portion (large diameter proximal portion) 411 of the inner coil 4, and the proximal end side of the truncated cone located at the most distal end (the proximal end side of the second truncated cone 26B in the fourth embodiment) of the combined truncated cone 26 by using a bonding member.

In the fourth embodiment, more preferably, the tapered middle portion 312 of the outer coil 30 and the tapered middle portion 412 of the inner coil 4 are arranged to be overlapped with each other, as shown in FIG. 6. By doing so, if the tapered middle portions 312, 412 are coaxial and have an approximately same tapered shape at the overlapped position, the rotation force transmitted from the large diameter side to the small diameter side of both the outer coil 30 and the inner coil 4 can be concentrated on the distal end side. Thus, the rotation transmission performance toward the distal end side can be more easily improved. In addition, the outer coil 30 and the inner coil 4 are densely wound from the proximal end to at least the middle joining section 5E. More preferably, from the proximal end to the distal end of the tapered middle portion are densely wound. In other words, the large constant diameter proximal portion 311 and the tapered middle portion 312 are densely wound in the outer coil 30, and the large constant diameter proximal portion 411 and the tapered middle portion 412 are densely wound in the inner coil 4. Furthermore preferably, an initial tension is applied to the densely wound portion.

Also in the first to third embodiments, although the inner coil 4 is not provided in these embodiments, the middle joining section 5D is preferably formed by connecting the densely wound large diameter side of the outer coil 30 and the large diameter side of the truncated cone located at the most distal side in the combined truncated cone 26 by using a bonding member. The densely wound large diameter side of the outer coil 30 is the second outer coil 32 in the first and second embodiments, and is the large constant diameter proximal portion (large diameter proximal portion) 311 of the second outer coil 320 in the third embodiment. The large diameter side of the truncated cone located at the most distal side in the combined truncated cone 26 is the proximal end side of the second truncated cone 26B in the first and third embodiments, and is the proximal end side of the third truncated cone 26C in the second embodiment.

If the second truncated cone 26B is completely included in the inner coil 4 in the length direction, the above described relational expression (3) is used. Even if only a part of the second truncated cone 26B is included in the inner coil 4, the relational expression (3) is used in the same way. Same as the above described relational expression (3), the following viewpoints can be used.

When the joint portion 28 (outer diameter D2) of the second truncated cone 26B is located at the proximal end side (rear end side) compared with the proximal end of the inner coil 4, and the outer diameter d of the second truncated cone 26B at a position connected with the inner coil 4 of the inner coil proximal joining section 5C is within the range of D2>d>D1, same as the relational expression (3), the outer diameter ratio d/D1 between the outer diameter d of the second truncated cone 26B at the position connected with the inner coil 4 and the minimum outer diameter D1 of the second truncated cone 26B, the outer diameter ratio A1/A2 of the inner coil 4, and the outer diameter ratio B1/B2 of the outer coil is preferred to be satisfy the following relational expression (4):

$$(d/D1)>(A1/A2)>(B1/B2) \quad (4).$$

By doing so, even if the outer diameter d of the second truncated cone 26B at the position connected with the inner coil 4 of the inner coil proximal joining section 5C is located at the small diameter side (distal end side) compared to the maximum outer diameter D2 (the joint portion 28 of the combined truncated cone 26) of the second truncated cone 26B satisfying the relation of D2>d>D1, the outer diameter ratio d/D1 is greater than the outer diameter ratio A1/A2 of the inner coil 4, the outer diameter ratio A1/A2 and the inner coil 4 is greater than the outer diameter ratio B1/B2 of the outer coil. Thus, the rotation transmission performance toward the distal end side can be improved.

The outer diameter ratio D2/D1 (or d/D1) of the truncated cone located at the most distal end in the combined truncated cone 26 is 1.50 to 4.20. The truncated cone located at the most distal end is the second truncated cone 26B in the first embodiment, and is the third truncated cone 26C in the second embodiment. The outer diameter ratio A1/A2 of the inner coil 4 is 1.15 to 2.80. The outer diameter ratio B1/B2 of the outer coil 30 is 1.10 to 1.80. The outer diameter ratio D2/D1 (or d/D1) of the truncated cone located at the most distal end is greater than the outer diameter ratio A1/A2 of the inner coil 4. The outer diameter ratio A1/A2 of the inner coil 4 is greater than the outer diameter ratio B1/B2 of the outer coil. Thus, the following relational expressions (3) and (4) are satisfied.

If the outer diameter ratios D2/D1 (or d/D1), A1/A2, B1/B2 are less than the above described range, the rotation angle of the proximal side is increased when the guide wire is rotated from the proximal end side to the distal end side. Thus, the torsional moment toward the distal end side is reduced and it becomes difficult to let the guide wire be inserted into the stenotic portion and the completely occluded lesion. If the outer diameter ratios exceed the above described range, although the rotation angle of the proximal side is reduced, the torsional moment is generated. In particular, torsional resistance of the small-diameter core connected with the inner coil 4 and torsional residence of the small-diameter inner coil 4 itself become insufficient. In such a case, the coil is not durable against high torsional moment and the coil starts to meander. This deteriorates the rotation transmission performance toward the distal end side.

In addition, a body part (e.g. cardiovascular and lower extremity vessels) to be treated, an inner vascular diameter, and practical dimensions of a medical tool (e.g. guiding catheter, balloon catheter and micro catheter) used for the radial dilation treatment are considered.

Thus, when the inner coil 4 and the outer coil 30 both having a tapered shape are simultaneously used, the torsional force, which is reduced by reducing the diameter of the distal end portion 2B of the core inserted into the inner coil 4, is further compensated. As a result, the rotation angle of the proximal side of the core is reduced, the bending rigidity and the buckling strength of the distal end of the combined truncated cone 26 of the distal end portion 2B of the core is increased, and the torsional moment toward the distal end side is increased. Therefore, the perforation performance of the completely occluded portion can be significantly improved.

In the present invention, when the total length of the outer coil is within the range of 20 mm to 350 mm, the distal end portion of the core inserted into the outer coil is preferably formed as the combined truncated cone by connecting at least two and equal to or less than 20 of the truncated cones, although it depends on the total length of the outer coil.

In the explanation of the third and fourth embodiments of the present invention, the shape of the outer coil 30 and the inner coil 4 is formed by the large constant diameter proximal portion (large diameter proximal portion) 311, 411, the tapered middle portions 312, 412 and the small constant diameter distal portions (small diameter distal portions) 313, 413 in order from the proximal end side to the distal end side. However, any shapes can be adopted as long as the large diameter proximal portion having a large outer diameter is formed on the proximal end side and the small diameter distal portion having a small outer diameter is formed on the distal end side.

Figure 7A:
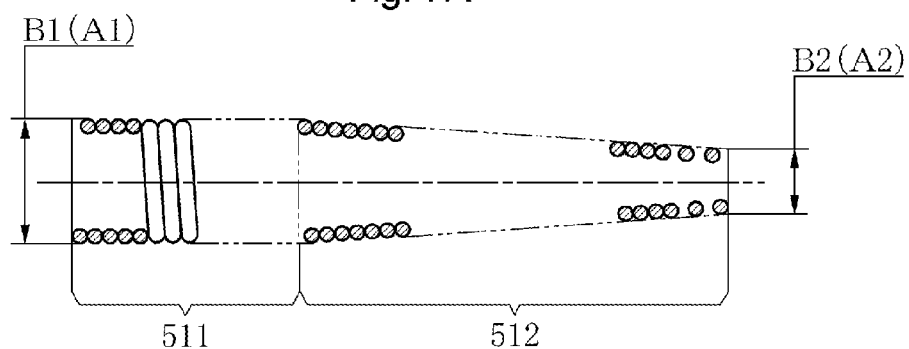
FIG. 7A to 7C show an outer coil and an inner coil of another embodiment of the present invention.
Figure 7B:
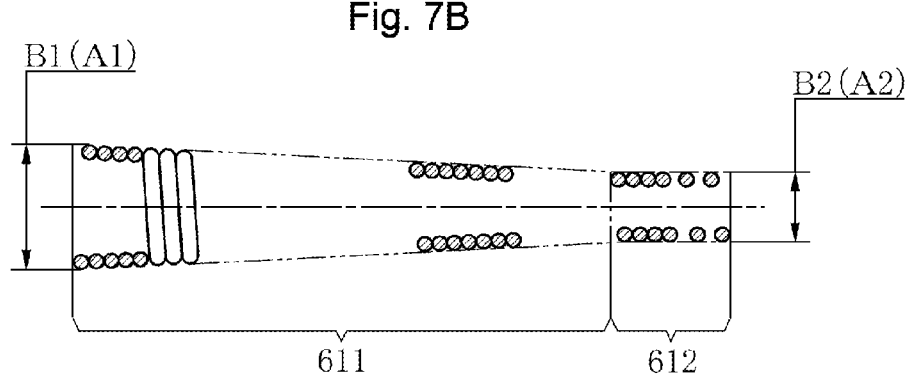
Figure 7C:
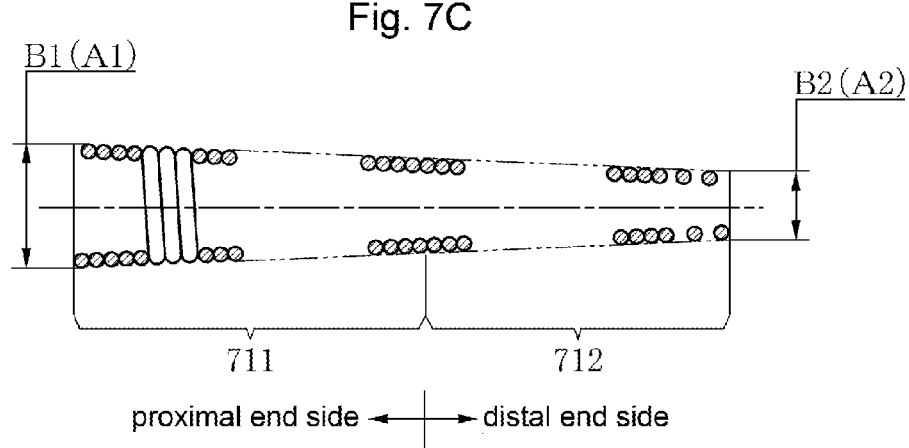

FIGS. 7A to 7C show other embodiments of the outer coil 30 and the inner coil 4. In FIG. 7A, a large diameter proximal portion 511 having a large constant outer diameter is provided on the proximal end side, and a small diameter distal portion 512 having an outer diameter gradually reducing toward the distal end side is provided on the distal end side. In FIG. 7B, a large diameter proximal portion 611 having an outer diameter gradually reducing from the proximal end side having a large diameter toward the distal end side is provided on the proximal end side, and a small diameter distal portion 612 having a small constant diameter is provided on the distal end side. In FIG. 7C, the outer diameter is gradually reduced from the proximal end side to the distal end side, and the coil is divided into two parts: a large diameter proximal portion 711 (a half in the total length) located on the proximal end side; and a small diameter distal portion 712 (the other half of the total length) located on the distal end side.

The outer coil 30 and the inner coil 4 can be formed by combining any shapes shown in FIGS. 7A to 7C or the shape described in the fourth embodiment. It is preferred that the outer coil 30 and the inner coil 4 have an approximately same tapered shape. In the above described embodiments, the outer diameter ratio B1/B2 of the outer coil 30 is calculated by using the maximum outer diameter of the proximal end side as the outer diameter B1 of the large diameter proximal portion and using the maximum outer diameter of the distal end as the outer diameter B2 of the small diameter distal portion. Similarly, the outer diameter ratio A1/A2 of the inner coil 4 is calculated by using the maximum outer diameter of the proximal end side as the outer diameter A1 of the large diameter proximal portion and using the minimum outer diameter of the distal end side as the outer diameter A2 of the small diameter distal portion.

As another embodiment, the coil structure shown in Japanese Patent No. 5517274 can be applied to the guide wire of the present invention, for example. In Japanese Patent No. 5517274, a first coil having a large constant diameter proximal portion, a tapered middle portion and a small constant diameter distal portion in order from the proximal end side to the distal end side, and a second coil arranged outside the tapered middle portion and the small constant diameter distal portion concentrically with them, wherein the distal end of the small constant diameter distal portion, the distal end of the core wire and the distal end of the second coil are connected with each other to form a distal joining section, and the proximal end of the second coil, an intermediate part of the first coil and the core wire are connected with each other to form a middle joining section.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A medical guide wire, comprising:
a core that has a portion gradually tapered in diameter from a proximal end side to a distal end side; and
an outer coil into which a distal end portion of the core is inserted, wherein
the distal end side of the outer coil is connected with the distal end side of the distal end portion of the core to form a distal joining section,
the proximal end side of the outer coil is connected with the proximal end side of the distal end portion of the core to form an outer coil proximal joining section,
the distal end portion of the core is a combined truncated cone formed by longitudinally connecting at least two truncated cones,
a longitudinal length of each of the truncated cones is reduced in order from the proximal end side to the distal end side,
an outer diameter ratio between a first maximum outer diameter of the proximal end side and a first minimum outer diameter of the distal end side in each of the truncated cones is increased in order from the proximal end side to the distal end side,
the outer diameter ratio is a ratio of the first maximum outer diameter of the proximal end side with respect to the first minimum outer diameter of the distal end side, and
when a second maximum outer diameter of the combined truncated cone is defined as D0, a second minimum outer diameter of the combined truncated cone is defined as D1, a total length of the combined truncated cone is defined as L, and an outer diameter Dm of the combined truncated cone at a position separated a distance X from a center in a cross section of the maximum outer diameter D0 to the core distal end of the combined truncated cone within a range of 0<X<L satisfies the following relational expression:

$$Dm > \{D0-(D0-D1)X/L\}.$$

2. The medical guide wire according to claim 1, wherein the outer coil includes a large diameter proximal portion and a small diameter distal portion in order from the proximal end side to the distal end side, and
when an outer diameter of the large diameter proximal portion of the outer coil is defined as B1, an outer diameter of the small diameter distal portion of the outer coil is defined as B2, and a third maximum outer diameter of the proximal end side of the truncated cone located at the most distal end side in the combined truncated cone is defined as D2, an outer diameter ratio (D2/D1) between the third maximum outer diameter D2 of the proximal end side and the second minimum outer diameter D1 of the distal end side in the truncated cone located at the most distal end side in the combined truncated cone is greater than an outer diameter ratio (B1/B2) of the outer coil satisfying the following relational expression:

$$\{(D2/D1) > (B1/B2)\}.$$

3. The medical guide wire according to claim 2, wherein an inner coil, which includes a large diameter proximal portion and a small diameter distal portion in order from the proximal end side to the distal end side, is provided outside the distal end portion of the core and inside the outer coil, the inner coil having a shorter longitudinal length than the outer coil and being arranged concentrically with the outer coil,
the distal end side of the small diameter distal portion of the inner coil is connected with the distal end side of the distal end portion of the core to form the distal joining section,
the proximal end side of the large diameter proximal portion of the inner coil is connected with the proximal end side of the distal end portion of the core to form an inner coil proximal joining section,
the combined truncated cone is formed by a first truncated cone and a second truncated cone in order from the proximal end side to the distal end side,
at least a part of the second truncated cone is arranged in the inner coil, and
when a third maximum outer diameter of the proximal end side of the second truncated cone is defined as D2, a third minimum outer diameter of the distal end side of the second truncated cone is defined as D1, an outer diameter of the large diameter proximal portion of the inner coil is defined as A1, and an outer diameter of the small diameter distal portion of the inner coil is defined as A2, an outer diameter ratio (D2/D1) of the second truncated cone is greater than an outer diameter ratio (D0/D2) of the first truncated cone satisfying the following relational expression: {(D2/D1)>(D0/D2)} and the outer diameter ratio (D2/D1) of the second truncated cone, an outer diameter ratio (A1/A2) of the inner coil and an outer diameter ratio (B1/B2) of the outer coil satisfy the following relational expression:

(D2/D1)>(A1/A2)>(B1/B2).

4. The medical guide wire according to claim 3, wherein the outer coil and the inner coil include a large constant diameter proximal portion, a tapered middle portion and a small constant diameter distal portion in order from the proximal end side to the distal end side, the tapered middle portion of the outer coil and the tapered middle portion of the inner coil are arranged to be overlapped with each other, the distal end side of the small constant diameter distal portion of the outer coil, the distal end side of the small constant diameter distal portion of the inner coil and the distal end side of the distal end portion of the core are connected with each other to form the distal joining section, the proximal end side of the large constant diameter proximal portion of the outer coil is connected with the proximal end side of the distal end portion of the core to form the outer coil proximal joining section, the proximal end side of the large constant diameter proximal portion of the inner coil is connected with the distal end portion of the core to form the inner coil proximal joining section, and the large constant diameter proximal portion of the outer coil, the large constant diameter proximal portion of the inner coil and the proximal end side of the second truncated cone are integrally connected with each other to form a middle joining section.

5. The medical guide wire according to claim 3, wherein the outer diameter ratio (D2/D1) of the truncated cone located at the most distal end side in the combined truncated cone is 1.50 to 4.20, the outer diameter ratio (A1/A2) of the inner coil is 1.15 to 2.80, and the outer diameter ratio (B1/B2) of the outer coil is 1.10 to 1.80.

6. The medical guide wire according to claim 4, wherein the outer diameter ratio (D2/D1) of the truncated cone located at the most distal end side in the combined truncated cone is 1.50 to 4.20, the outer diameter ratio (A1/A2) of the inner coil is 1.15 to 2.80, and the outer diameter ratio (B1/B2) of the outer coil is 1.10 to 1.80.

* * * * *